United States Patent [19]

Sarvazyan et al.

[11] Patent Number: 5,706,815
[45] Date of Patent: Jan. 13, 1998

[54] METHOD AND DEVICE FOR MEASURING ANISOTROPIC MECHANICAL PROPERTIES OF TISSUE

[76] Inventors: Armen Sarvazyan, 22 Landsdowne Rd., East Brunswick, N.J. 08816; Mark E. Schafer, 165 Percy Ct., Norristown, Pa. 19401; Viktor Ponomarev, 25 Krasnykh Zor, Apt. 35, Rostov-on-Don, Russian Federation

[21] Appl. No.: 721,906

[22] Filed: Sep. 27, 1996

Related U.S. Application Data

[60] Provisional application No. 60/004,350, Sep. 27, 1995.

[51] Int. Cl.⁶ ........................................ A61B 8/00
[52] U.S. Cl. ..................... 128/660.02; 128/774; 73/579
[58] Field of Search ........................ 128/774, 660.02, 128/661.07; 73/575, 579, 648, 645

[56] References Cited

U.S. PATENT DOCUMENTS

| | | | |
|---|---|---|---|
| 4,144,877 | 3/1979 | Frei et al. | 128/2 S |
| 4,177,798 | 12/1979 | Leveque et al. | 128/774 |
| 4,396,025 | 8/1983 | De Rigal et al. | 128/774 |
| 4,771,792 | 9/1988 | Seale | 128/774 |
| 4,777,599 | 10/1988 | Dorogi et al. | 364/413.02 |
| 4,947,851 | 8/1990 | Sarvazyan et al. | 128/660.02 |
| 5,099,848 | 3/1992 | Parker et al. | 128/661.07 |
| 5,115,808 | 5/1992 | Popovic et al. | 128/660.02 |
| 5,143,072 | 9/1992 | Kantorovich et al. | 128/660.02 |
| 5,195,521 | 3/1993 | Melton, Jr. et al. | 128/660.02 |
| 5,313,946 | 5/1994 | Melton, Jr. | 128/660.02 |
| 5,533,402 | 7/1996 | Sarvazyan et al. | 73/645 |

FOREIGN PATENT DOCUMENTS 2173896  10/1986  United Kingdom.

OTHER PUBLICATIONS

Finlay, B., "Dynamic Mechanical Testing of Human Skin 'In Vivo'", *J. Biomechanics*, 1970, 3, 557–568.

Clark, J.A. et al., "Mechanical Characterisation of Human Postburn Hypertrophic Skin During Pressure Therapy", *J. Biomechanics*, 1987, 20(4), 397–406.

Thacker, J.G. et al., "In vivo extensometer for measurement of the biomechanical properties of human skin", *Rev. Sci. Instrum.*, 1977, 48, 181–185.

Sarvazyan, A.P., "Development of methods of precise ultrasonic measurements in small volumes of liquids", *Ultrasonics*, 1982, 151–154.

Patent Cooperation Treaty International Search Report dated Jan. 31, 1997, Int'l Application No. PCT/US96/15563.

*Primary Examiner*—Marvin M. Lateef
*Assistant Examiner*—Derrick Fields
*Attorney, Agent, or Firm*—Woodcock Washburn Kurtz Mackiewicz & Norris LLP

[57] ABSTRACT

A device and method for measuring the anisotropic mechanical properties of tissue is provided. The device comprises a flexural resonator driven by a transducer to oscillate at a plurality of angles of oscillation while in contact with a tissue to be analyzed. The resonance frequencies and resonance peak widths for the flexural resonator are measured at each of the plurality of angles of oscillation. Based on these values and the free state resonance frequency of the oscillating flexural resonator, anisotropic mechanical properties of the tissue are derived. A pressure normalizing element is utilized to ensure secure and standardized contact between the flexural resonator and the tissue during the measurements. The method of the present invention provides for determining these anisotropic mechanical properties by measuring the free state resonance frequency of the flexural resonator, measuring the resonance frequencies and resonance peak widths for the resonator at a pluality of angles of oscillation while in contact with a tissue, calculating the mechanical properties corresponding to each of the angles of oscillation, and displaying these values in a useful manner. The method may be implemented as software by a microprocessor.

17 Claims, 12 Drawing Sheets

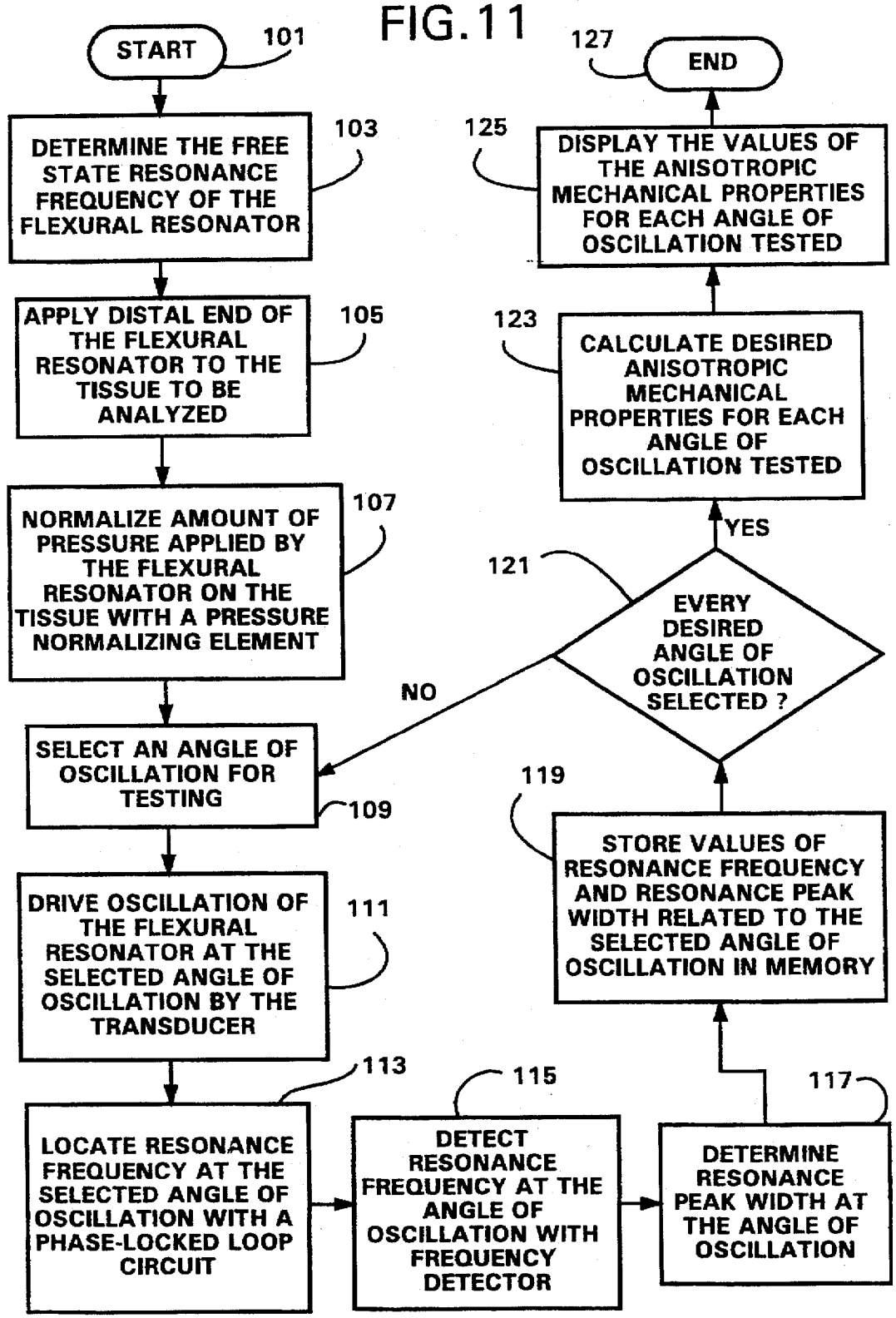

METHOD AND DEVICE FOR MEASURING ANISOTROPIC MECHANICAL PROPERTIES OF TISSUE

This application claims priority from U.S. Provisional application Ser. No. 60/004,350, filed Sep. 27, 1995, herein incorporated by reference in its entirety.

FIELD OF THE INVENTION

The present invention relates to a device and method for analyzing an area of tissue to determine certain mechanical properties of the tissue. More specifically, the invention relates to a device and method in which an oscillating flexural resonator is applied to a surface of the tissue being analyzed and caused to oscillate at specified angles of oscillation upon the surface of the tissue such that the resonance frequency and the resonance peak width of the oscillating resonator at each angle of oscillation is determined and used to calculate mechanical properties of the tissue for that angle of oscillation.

BACKGROUND OF THE INVENTION

Determining the mechanical properties of tissue is useful in many medical, cosmetological and food preparation applications. In particular, human tissue, more precisely skin, has been analyzed by a number of devices and methods which attempted to determine certain properties of the skin. Examples of prior art patents in which some property of skin is determined include U.S. Pat. Nos. 5,115,808 to Popovic et al., 4,947,851 to Sarvazyan et al., 4,777,599 to Dorogi et al., 4,396,025 to De Rigal et al., 4,177,798 to Leveque et al., and UK Patent Application 2,173,896A to L'Oreal. The properties generally investigated in tissue include mechanical impedance, elasticity and viscosity.

The results of the analyses of tissue properties are most often utilized in conjunction with medical applications. The result of the analysis can be used, for example, in determining the effects of scar management techniques on hypertrophic scar development and resolution, in documenting body regions with increased elasticity which might be used as reconstructive flaps, and in monitoring changes in skin stiffness during therapies using, for example, moisturizers, retinoids, or steroids. Such measurements are also used in dermatology for quantitative characterization of normal and diseased skin states, for assessment of wound healing and for monitoring skin grafts and pressure sores, for quantifying the effects of scar management techniques on development of keloid and hypertrophic scars, and for monitoring therapy and diagnosing various skin diseases accompanied by changes in elasticity of skin. In plastic surgery, the measurements are used for evaluating the effects of facial rejuvenation surgery on the state of the skin in older patients.

The properties of the skin can be important in analyzing the phenomenon of aging, and in learning more about diseases such as psoriasis and mycosis fungoides, and the formation of infiltration lesions, and inflammations. Moreover, these properties can be used to characterize various states of the skin such as degrees of tension, dryness, or softness. They can be used to evaluate short and longer term changes in the tissue resulting from medications, pharmaceuticals, and ointment applications and the effect of detergents or skin conditioning substances in revitalizing disturbed or damaged skin. Finally, the knowledge of skin isotropy is useful to surgeons in choosing optimum directions for dissecting the skin during operations.

Beyond the obvious benefits of determining mechanical properties of human tissue, the same properties of mechanical impedance, shear elasticity and dynamic viscosity are present in different biological, or even non-biological tissues. Knowledge of the anisotropic mechanical properties can be useful in a variety of applications. For example, in analyzing the mechanical properties of a piece of meat, determinations on grading, aging, tenderization or required processing can be made more easily and accurately. Furthermore, as it is well known in the art, the mechanical properties of food products, capable of being determined by the present invention, are closely related to the quality of the food product. For example, the ripeness, or freshness of a food product can often be determined by analyzing the mechanical properties of the tissue of the food product, such as elasticity, or hardness.

In the prior art, all of the devices that were developed to obtain information on the mechanical properties of the tissues for medical applications were bulky and, therefore, inconvenient to use. They required that the tissue being analyzed be deformed by various means, such as stretching in different directions, which could result in substantial discomfort to a patient or injury to the tissue. They also often involved temporary fixtures being applied to the skin or were applicable only for excised samples of tissue. In order to measure anisotropy, all of the prior art devices had to be physically manipulated by manually aligning them in different directions and taking measurements at the various directions.

SUMMARY OF THE INVENTION

The present invention is a device and method for measuring the mechanical properties of anisotropic tissue in a plurality of directions by a single application of the device of the present invention to an area of tissue to be analyzed. The tissue analyzer of the present invention comprises a flexural resonator having a distal end which is to be applied perpendicular to and in contact with the surface of tissue being analyzed. The flexural resonator also has a base with a transducer, which drives and supports oscillation of the flexural resonator at a plurality of angles of oscillation. In a preferred embodiment, the transducer is a piezotransducer, radially polarized with two pair of electrodes affixed to an outer surface of a piezoceramic tube, such that when a voltage is applied to the electrodes, the transducer causes the flexural resonator to oscillate in a plane perpendicular to the surface of the tissue at a specific angle of oscillation.

The tissue analyzer also comprises an electrical module containing a processor unit, typically an 8-bit microprocessor, for transmitting voltage signals to the electrodes of the transducer, and for receiving feedback regarding the resonance frequency of the flexural resonator at each angle of oscillation. The processor unit also acts as a calculating means by performing calculations which are used in determining the specific mechanical properties of the tissue being analyzed. The electrical module also contains a memory unit for storing data and instructions for use by the processor means. There is also a phase-locked loop circuit integrated into the electrical module which controls the transducer and drives the oscillation of the flexural resonator at the resonance frequency for each angle of oscillation based upon feedback from the electrodes of the transducer. Additionally, the electrical module comprises a display which receives data from the processor unit and displays the data either graphically or in text. Furthermore, the tissue analyzer comprises connecting cables for connecting the electrical module, including the processor unit and phase-locked loop circuit to the transducer at the base end of the flexural resonator.

Preferably, the device of the present invention also comprises a pressure normalizing element. The pressure normalizing element is used to ensure that the distal end of the flexural resonator maintains a secure connection with the surface of tissue being analyzed, and to standardize the amount of force applied by the distal end of the flexural resonator to the surface of tissue being analyzed. In one preferred embodiment, the pressure normalizing element comprises a support ring surrounding the distal end of the flexural resonator and at least one pressure ring, wherein the support ring is supported by a spring such that the measurements are only taken when the pressure ring is applying a predefined amount of pressure to the tissue being analyzed. In another preferred embodiment, the pressure normalizing element comprises a suction pump which applies negative pressure to the surface of tissue being analyzed thereby pulling the tissue into a secure connection with the distal end of the flexural resonator and standardizing the force applied by the flexural resonator to the tissue. In yet another embodiment, preferably for use with non-human tissue, the pressure normalizing element comprises a sharp element, or needle, affixed to the distal end of the flexural resonator, wherein the needle is inserted into the tissue to be analyzed such that a secure connection is made.

The method of the present invention comprises the steps of oscillating a flexural resonator with a transducer located at a base end of the flexural resonator and determining a free state resonance frequency of the oscillating flexural resonator. The next step is to place a distal end of the oscillating flexural resonator on a surface of tissue to be analyzed. Then, the method provides for measuring a modified resonance frequency and a resonance peak width for the oscillating flexural resonator at a plurality of angles of oscillation upon the surface of tissue being analyzed. The method continues by determining anisotropic mechanical properties of the area of tissue being analyzed based on the modified resonance frequencies and resonance peak widths measured for the oscillating flexural resonator at the plurality of angles of oscillation. The anisotropic properties, including mechanical impedance, shear elasticity and dynamic viscosity, are calculated according to known formulas once the modified resonance frequencies and resonance peak widths are determined at the plurality of angles of oscillation. Finally, the method of the present invention provides for displaying the calculated properties at each of the plurality of angles of oscillation in either a graphical representation, or in a textual format.

BRIEF DESCRIPTION OF THE DRAWINGS

A full understanding of the invention can be gained from the following description of a preferred embodiment when read in conjunction with the accompanying drawings in which:

FIG. 11 is a flowchart demonstrating the steps of the method of the present invention.

DETAILED DESCRIPTION OF PREFERRED EMBODIMENTS

A method and system that overcome the above-mentioned problems associated with measuring the anisotropic mechanical properties of tissue are described below with reference to the figures. Those skilled in the art will readily appreciate that the description given herein with respect to the figures is for explanatory purposes only and is not intended in any way to limit the scope of the invention. Also, common reference numbers are used throughout the drawings to represent common elements. All questions regarding the scope of the invention should be resolved by referring to the appended claims.

Figure 1:
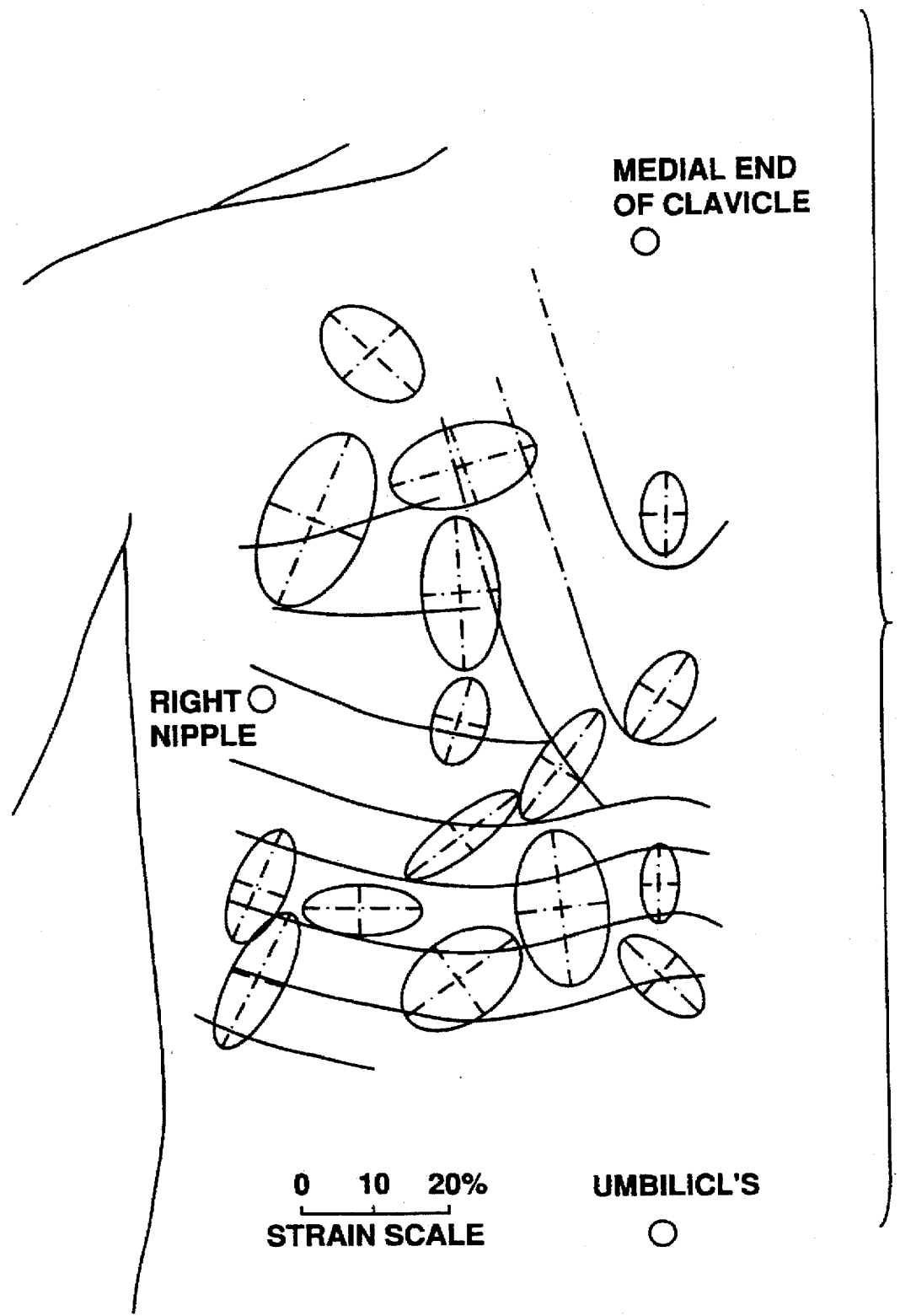
FIG. 1 is an illustration of the anisotropic properties of various surfaces of tissue on a human body.

Referring now to the figures, FIG. 1 shows an average area of tissue, here the skin on a human chest, wherein the natural anisotropic properties of the skin are displayed by the ellipses which show extensibility of the skin in varying directions. This figure and discussion on the anisotropic properties of skin can be found in Finlay, "Dynamic Mechanical Testing of Human Skin 'In Vivo'", Vol. 3 J. Biomechanics at pp. 557–568 (1970), herein incorporated by reference. This figure explains the necessity of the present invention in accurately describing the properties of human tissue, which vary based on the direction of measurement. The benefit of the present invention is that a single application of a tissue analyzer device can produce information relating to the mechanical properties of the tissue being analyzed in any direction. The method and device of the present invention eliminate the need for multiple applications of a device upon a surface of tissue where the device must be aligned in a particular direction in order to obtain results on the properties of the tissue corresponding to that direction. There are a number of prior art devices which required this type of manipulation in order to measure anisometric properties, such as those discussed in Thacker, "In vivo extensometer for measurement of the biomechanical properties of human skin", Vol. 48 Rev. Sci. Instrum. at pp. 181–182 (1977), herein incorporated by reference. The present method and device also eliminate the need to manipulate or stretch the area of tissue being analyzed. The present invention, therefore, provides information on the anisotropic mechanical properties, including mechanical impedance, shear elasticity and dynamic viscosity, of the tissue being analyzed in a multitude of direction. Although FIG. 1 displays the presence of anisotropic properties, such as those intended to be measured by the present invention, on an area of tissue, or skin, on a human body, the tissue to be analyzed by the present invention is not so limited. Tissue is herein defined as any substrate, whether biologic or not, that can possess the anisotropic mechanical properties intended to be determined by the present invention. Substrates which are intended to be within the definition of tissue and other viscoelastic material include, but are not limited to, skin or other biological tissue and structures, meat or food products, including meats, fish, poultry, cheeses, fruits, and vegetables, rubber or any viscoelastic material, plastics, and organic or inorganic polymers.

Figure 2:
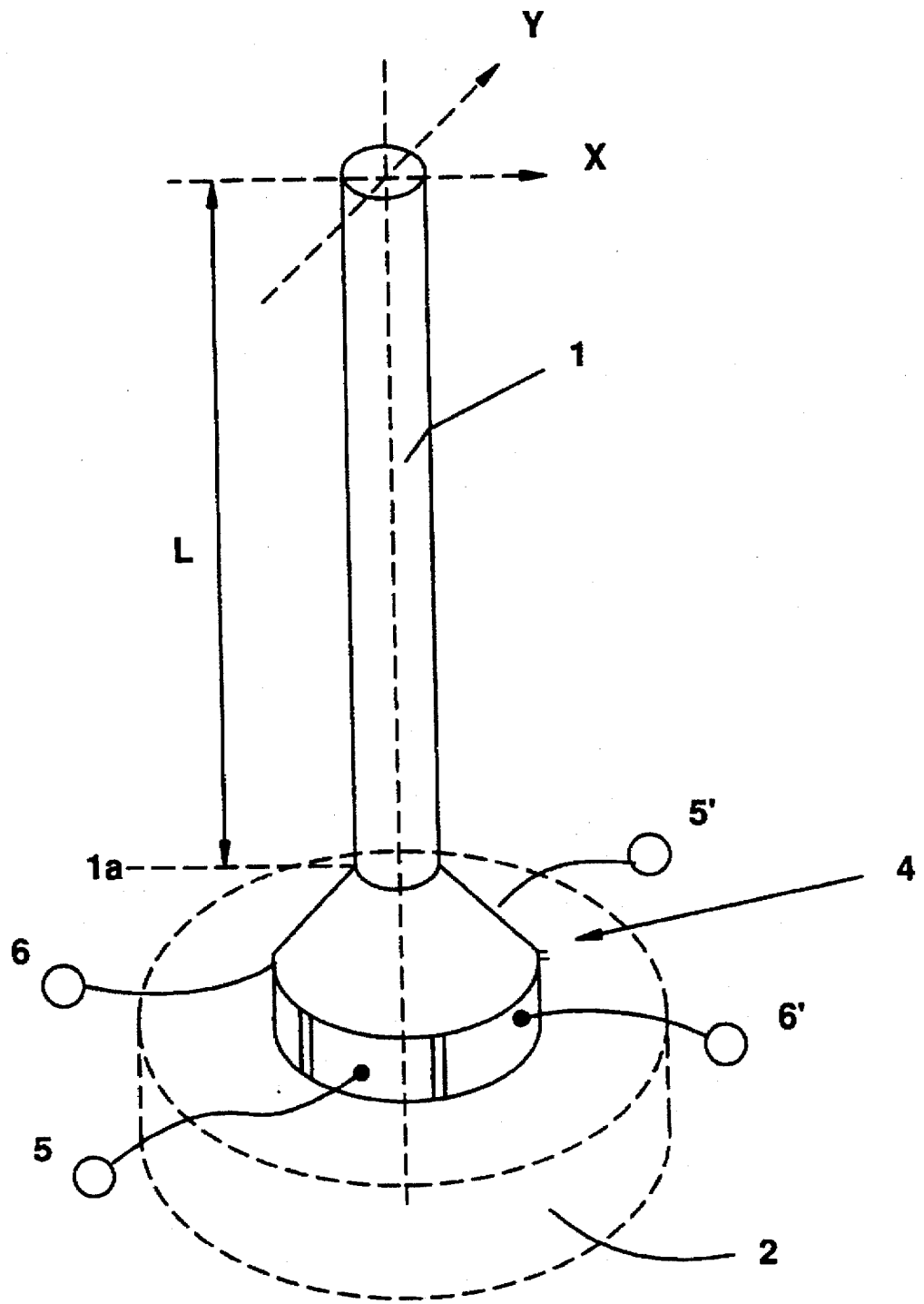
FIG. 2 is an illustration of a flexural resonator of the present invention with the transducer containing a plurality of electrodes.

Referring now to FIG. 2, the flexural resonator of the present invention is shown. The flexural resonator comprises a cantilever which oscillates in a bending motion, and can be equated to half of a tuning fork. The cantilever oscillations are driven and supported by a transducer, which is attached at the base of the cantilever. In a preferred embodiment, the flexural resonator comprises a metal rod 1, which is cylindrical in shape. The metal rod 1 is preferably composed of titanium. In an embodiment that has been used, the titanium rod is 20 mm long with a diameter of 2 mm. This rod possesses a resonance frequency of approximately 4 kHz. In some embodiments of the present invention, the resonance frequency of the flexural resonator when in contact with tissue being analyzed is between 0.5 and 10 kHz. In human tissue, the resonance frequency is generally between 3 and 5 kHz. Referring again to FIG. 2, the distal end of the metal rod 1 is shown with an x- and y-axis representing the plane of contact with the surface of tissue 3 (not shown) to be measured.

At the other end of the metal rod 1, is a base end 1a. The base end 1a is affixed to a transducer 4, which will be described in more detail below in connection with FIG. 5. Generally, the transducer 4, or more than one transducer, is used to control the oscillation of the flexural resonator based upon certain inputs. In the present invention, the transducer 4 causes the metal rod 1 to oscillate in a particular plane of oscillation. The inputs to the transducer 4 can be used to select the angle of the plane of oscillation, referred to hereinafter as the angle of oscillation $\phi$. This allows the device of the present invention to determine the anisotropic mechanical properties of the tissue being analyzed in a plurality of directions without removing the device from the tissue 3 or repositioning the device on the tissue 3. This was not possible with any prior art tissue analyzing device.

In a preferred embodiment, the transducer 4 is a radially polarized tubular piezotransducer. Examples of piezoceramic tubes suitable for use in the transducer 4 of the present invention include the PZT-5H tubes by Valpey-Fisher (Hopkinton, Mass.) and the EBL #3 tubes by Staveley Sensors Inc. (East Hartford, Conn.). These are particularly chosen because of their strong piezoelastic qualities. Affixed around the outer surface of the tubular piezotransducer are a plurality of electrodes. In FIG. 2, representing a preferred embodiment, there are two pair of electrodes used in controlling the transducer 4 and thus the oscillation of the metal rod 1 of the flexural resonator. One pair of electrodes are transmitting electrodes 5, 6 and one pair are receiving electrodes 5', 6'. When voltages are applied to the two transmitting electrodes 5, 6, the metal rod 1 of the flexural resonator oscillates in a particular direction based on the ratio of the voltages applied to the two transmitting electrodes 5, 6. Other transducer means or configurations for the transducer element will be readily apparent to those skilled in the art, and include, for example, affixing four separate piezotransducers around the base end of the flexural resonator to drive the flexural resonator in any chosen direction of oscillation.

Figure 3:
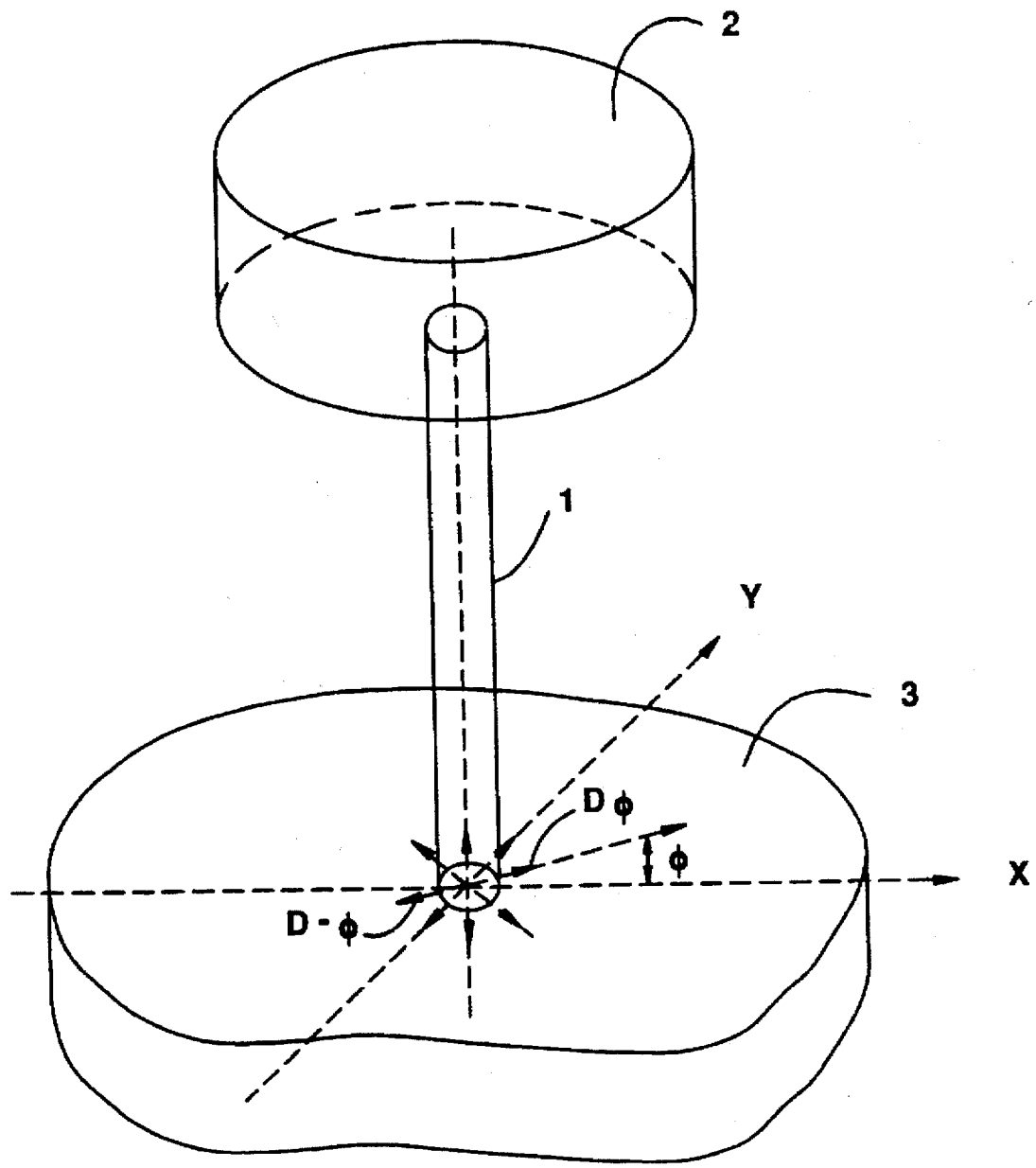
FIG. 3 shows a flexural resonator in contact with a surface of tissue oscillating at a particular angle of oscillation.

FIG. 3 depicts the same flexural resonator displayed in FIG. 2, but inverted such that the distal end of the metal rod 1 is being applied to an area of tissue 3. Again, the transducer 4 (not shown), affixed to the base end 1a of the flexural resonator excites and drives an oscillation of the cantilever, or metal rod 1. The x- and y-axes indicating the plane of the surface of tissue 3 being analyzed are clearly shown. By referring to FIG. 3, the angle of oscillation $\phi$ can be more clearly defined. As shown in FIG. 3, when performing the method of the present invention, the flexural resonator is applied to the tissue 3 being analyzed with the distal end of the metal rod 1 generally perpendicular to the plane of the tissue 3, indicated by the x- and y-axes. The transducer 4 causes the metal rod 1 to oscillate in a plane z which is perpendicular to the x-y plane of the tissue 3. The direction of the oscillation, however, may be measured by the angle which the plane of oscillation z forms with the x-axis on the tissue 3. One example of this angle of oscillation $\phi$ is represented on the figure with the same symbol. When the angle of oscillation $\phi$ is as it is shown in FIG. 3, the direction in which the metal rod 1 is oscillating is represented by the arrows labeled $D_\phi$ and $D_{-\phi}$. Obviously, the plane of oscillation z resulting from the oscillation of the metal rod 1 can form any angle with the x-axis from 0 to 180 degrees, wherein 0 or 180 degrees would indicate oscillation of the metal rod 1 along the x-axis and 90 degrees would indicate oscillation of the metal rod 1 along the y-axis. The transducer 4 can be manipulated to produce any desired angle of oscillation $\phi$. This will be explained more fully in connection with FIGS. 5, 6a and 6b below.

Figure 4:
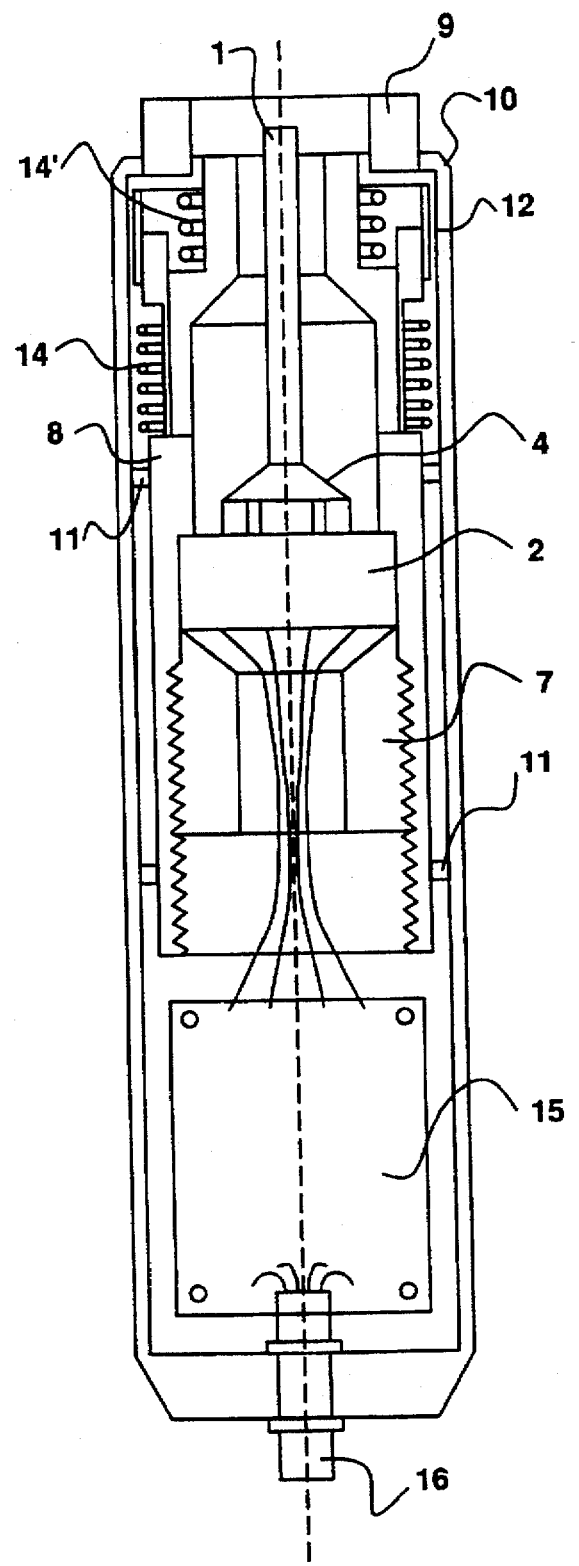
FIG. 4 is a cross-sectional view of a device of the present invention.

While the flexural resonator shown in FIGS. 2 and 3 is a component of the device of the present invention, a preferred embodiment of an entire tissue analyzer is disclosed in FIG. 4. The flexural resonator with its metal rod 1 and transducer 4 is enclosed within a small, portable outer case 10. The case 10 also holds a small PC board 15 carrying input amplifiers, connecting cables 32 and various support structures. In a preferred embodiment, a pressure normalizing element is also an important feature of the tissue analyzer. The pressure normalizing element functions to ensure a constant, standardized connection between the distal end of the metal rod 1 and the area of tissue 3 being analyzed. The pressure normalizing element standardizes the force or pressure exerted by the metal rod 1 against the tissue 3, so that variations in pressure do not affect the values obtained relating to the anisotropic mechanical properties of the tissue 3. The pressure is preferably normalized at some pressure between 10 and 500 grams, depending on the material being analyzed. Again, in human tissue, the pressure is preferably between 150 and 200 grams. While the components comprising one embodiment of the pressure normalizing element are shown in FIG. 4, they will be discussed more fully below in connection with FIGS. 8-10, which show more detailed diagrams of the various pressure normalizing elements which are capable of performing the desired function.

Referring again to FIG. 4, a support ring 8 is attached to the tissue analyzer's outer case 10 by a plurality of rubber rings 11. The support ring 8 and the fixture 7 are used to provide firm attachments of the metal rod 1 and the transducer 4 within the outer case 10 of the tissue analyzer. Connecting the flexural resonator to the support ring 8 is a support base 2. The support base 2 is preferably composed of a heavy solid metal material which is useful in isolating the flexural resonator and preventing external forces from affecting its oscillation. The support base 2 and support ring 8 both also ensure that the connecting cables 32 which transmit data and signals between the transducer 4 and an electrical module external to the outer case 10 or the PC board 15 are not dislodged by movement of these components in relation to each other. The PC board 15 contains input amplifiers. External to the hand-held device is the electrical module containing a microprocessor 30, a display unit 31 and a circuit for use in performing the method of the present invention. The circuit diagram and the operation of the electronic components in the tissue analyzer device will be explained more fully below in connection with FIGS. 5, 6a and 6b. Briefly, signals from the components in the electrical module, primarily originating in the microprocessor 30, are transmitted to the transmitting electrodes 5, 6 of the transducer 4 in the flexural resonator. These signals can determine the angle of oscillation at which the anisotropic mechanical properties of the area of tissue 3 are to be calculated. The resonance frequency $F_R$ of the metal rod 1 at the chosen angle of oscillation $\phi$ is determined by using a phase-locked loop circuit and a frequency detector. The performance and design of the phase-locked loop circuit is generally known to those skilled in the art, and the circuits are commercially available, for example, the IC MAX038 from the Digi Key catalog. Once the phase-locked loop circuit drives the metal rod 1 of the flexural resonator to oscillate at the resonance frequency for the specified angle of oscillation $\phi$, the resonance frequency $F_R$ and the resonance peak width $\delta F$ are measured. These values are then transmitted to the microprocessor 30, and are stored in memory 33. The microprocessor 30 can then compute the values of the desired mechanical properties for the particular angle of oscillation $\phi$ based on the resonance frequency $F_R$, the resonance peak width $\delta F$, the free state resonance frequency $F_0$ of the metal rod 1, and the formulas provides below. Finally, the tissue analyzer device has a connecting cable 16 for receiving and transmitting signals and data to and from the components within the outer case 10 of the hand-held probe and the components within the external electrical module.

Figure 5:
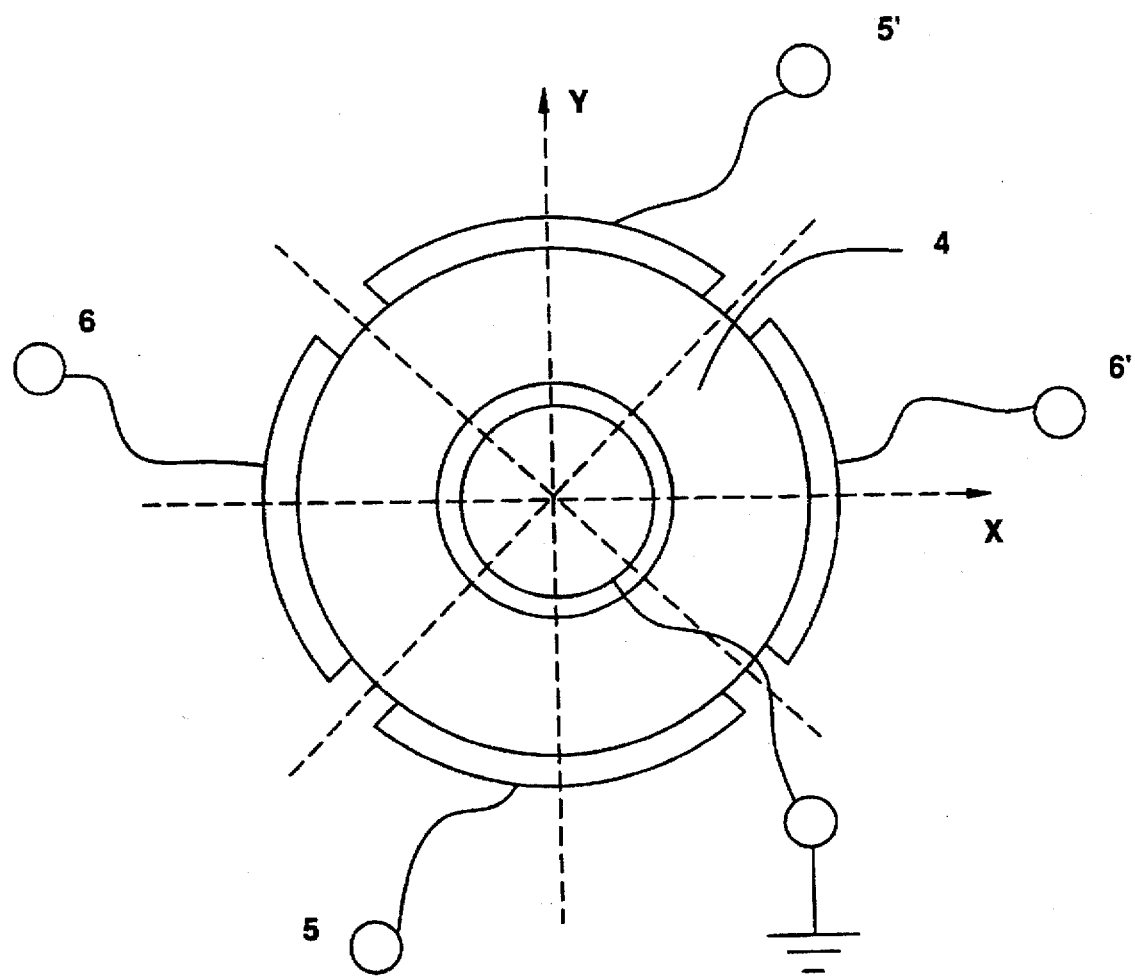
FIG. 5 shows the arrangement of electrodes in a transducer.
Figure 6A:
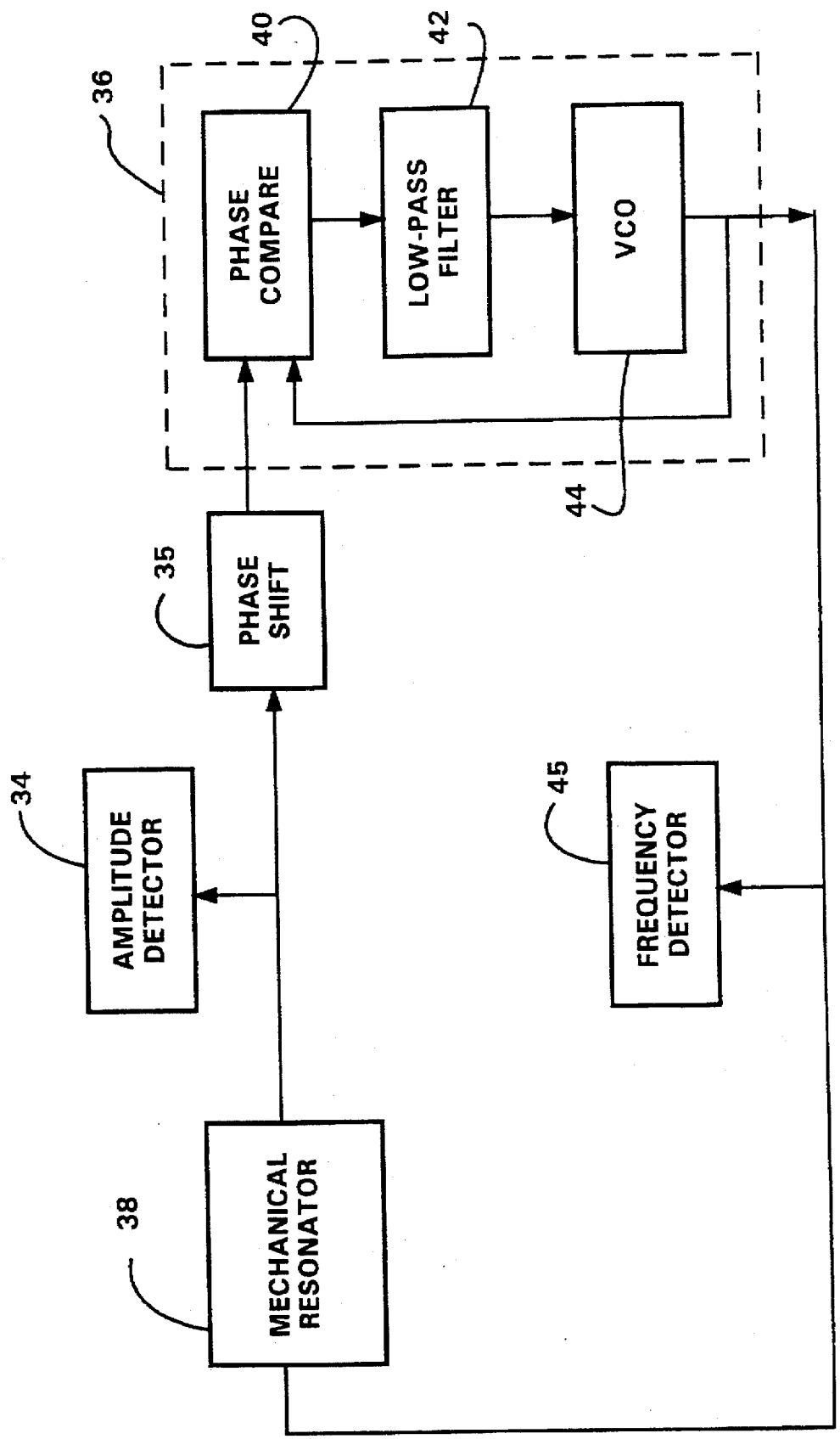
FIGS. 6a and 6b show circuit diagrams, including a phase-locked loop circuit, for use in the present invention.
Figure 6B:
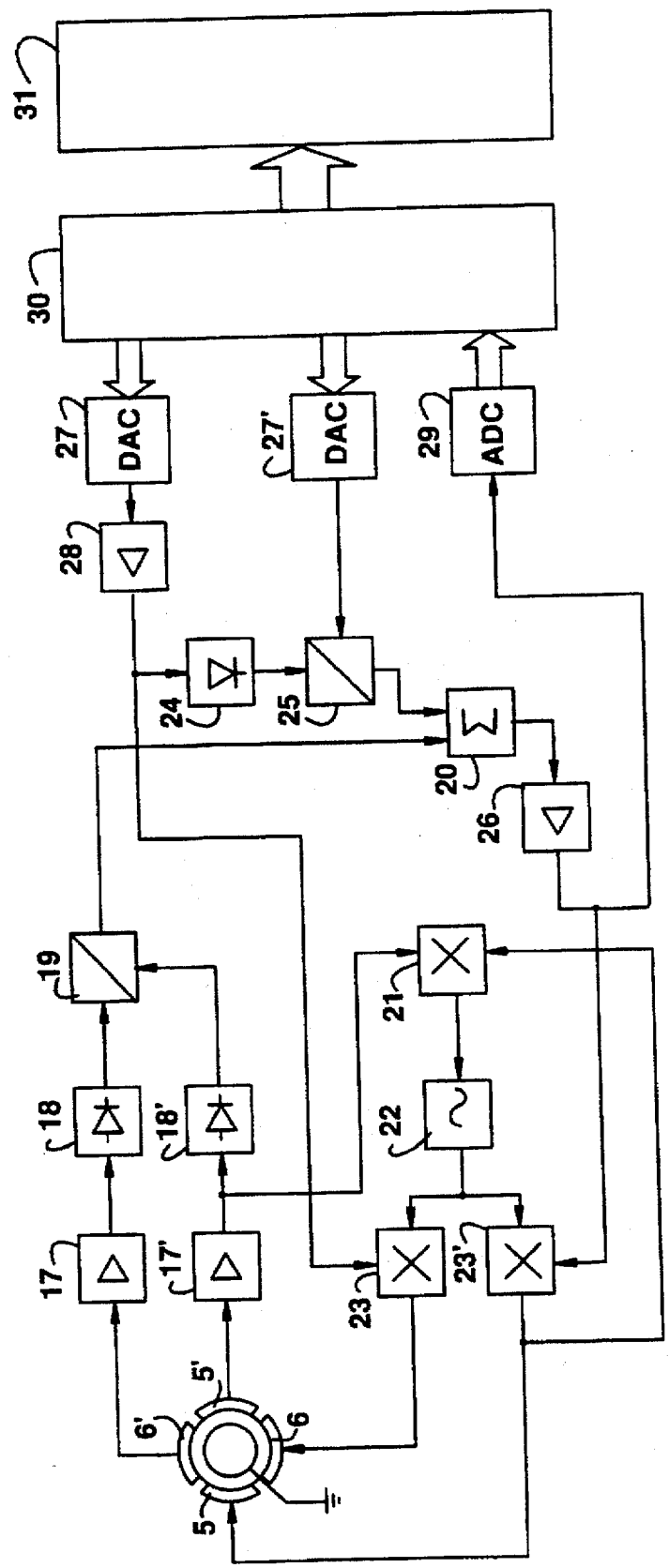
Figure 7:
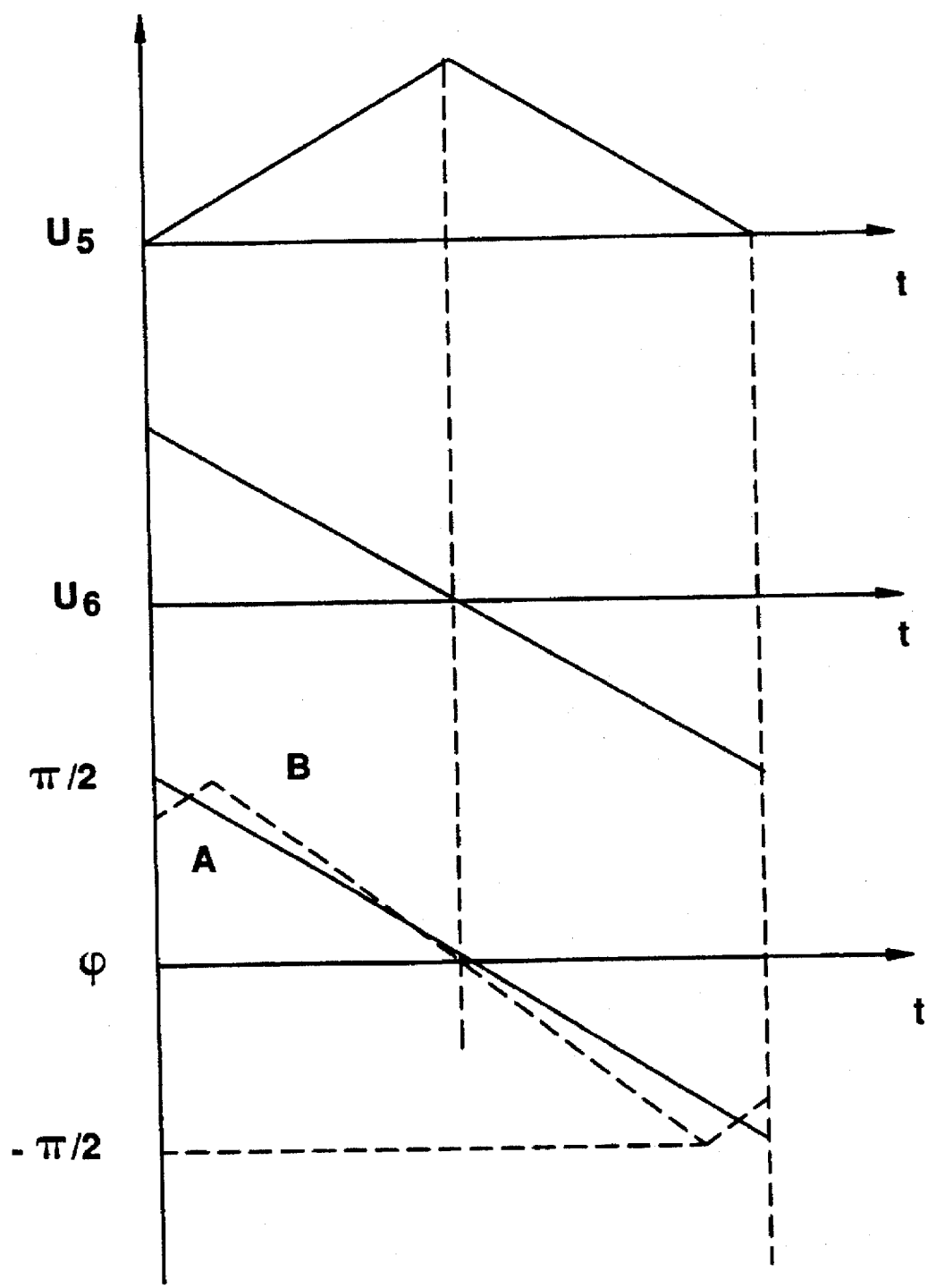
FIG. 7 is a graph showing values of the angle of oscillation resulting from the application of voltages to electrodes of a transducer in both isotropic and anisotropic tissue.

FIG. 5 is a more detailed depiction of a preferred embodiment of the transducer 4 for use in the present invention. The tubular piezoceramic material, indicated by the shaded area, separates the grounded inner ring and the four electrodes 5, 6, 5', and 6'. Again, two of the electrodes are transmitting electrodes 5, 6 and two are receiving electrodes 5', 6'. In a preferred embodiment, each of the electrodes is connected to a phase-locked loop and frequency detector circuit, as shown in FIGS. 6a and 6b. Furthermore, the transmitting electrodes 5, 6 receive signals from the microprocessor 30 which control the angle of oscillation $\phi$. These connections are made by the connecting cable 16.

FIG. 6a is a block representation of the electronic circuitry required by the present invention, but is sufficient, based on the well-known applications of the named components, to enable those skilled in the art to implement the necessary circuitry. The details of the connections between the electrodes 5, 5', 6, 6' of the transducer 4 and the electronic circuitry are shown in FIG. 6b. As shown in FIG. 6a, a basic phase-locked loop circuit 36 is used to drive the mechanical resonator 38 to oscillate at its resonance frequency for a given angle of oscillation $\phi$. The basic components of the phase-locked loop circuit 36 are a phase comparator 40, a low-pass filter 42 and a voltage controlled oscillator (VCO) 44, as shown. The typical resonator control circuit also has an amplitude detector 34 and a phase shifter 35 connected in series with the phase-locked loop circuit 36. A frequency detector 45 then measures the value of the resonance frequency for that angle of oscillation $\phi$ and transmits that data to the microprocessor 30, shown in FIG. 6b.

When performing the method of the present invention, the free state resonance frequency $F_0$ of the resonator must be known in order to complete the necessary calculations. Therefore, before the distal end of the metal rod is applied to an area of tissue 3 to be measured, the free state resonance frequency $F_0$ of the oscillating rod 1 is determined with the same phase-locked loop cirucitry discussed above. To ensure the most precise evaluation, the free state resonance frequency $F_0$ should be determined immediately before placing the flexural resonator on the tissue 3 to be analyzed. This prevents conditions at the test location which may alter the free state resonance from adversely affecting the testing. The value of the free state resonance frequency $F_0$ is then stored in a memory unit 33 for use by the microprocessor 30. A less accurate approach would be to simply store the value of the free state resonance frequency $F_0$ in memory and treat that value as a constant, thereby avoiding the step of determining the free state resonance frequency $F_0$ before every test. This would also be an acceptable approach, though somewhat less accurate.

When the flexural resonator is used to determine the anisotropic mechanical properties of a particular area of tissue, the distal end of the metal rod 1 is applied to a surface of tissue 3, as shown in FIG. 3. The microprocessor 30 then selects the angle of oscillation $\phi$ at which the properties are to be determined. In performing the method of the present invention, the angle of oscillation $\phi$ will be varied such that the mechanical properties are determined over the entire range of angles, 0 to 180 degrees. The angle of oscillation $\phi$ is defined by the ratio of voltages at the transmitting electrodes 5, 6. After the microprocessor 30 transmits the necessary signals to the electrodes to drive the oscillation of the flexural resonator at a selected angle of oscillation $\phi$, the phase-locked loop circuit 36 drives the oscillation caused by the transducer 4 to the resonance frequency of the flexural resonator for the selected angle of oscillation $\phi$.

The phase-locked loop 36 can also be used to determine the resonance peak width, $\delta F$, by locking on phases that are 45 degrees out of phase with the resonance frequency phase. The resonance frequency $F_R$, for example, is always located at the 90 degree phase shift. Therefore, when the phase-locked loop locks on the 90 degree phase shift at a given angle of oscillation $\phi$, the frequency measured by the frequency detector 45 is the resonance frequency $F_R$ for that angle. When the phase-locked loop locks on a phase of +45° or −45°, however, the frequencies measured correspond to the half power bandwidth of the resonance peak. $\delta F$ can then be calculated using the formula $\delta F = (F_{+45} - F_{-45})/2$.

As described above, the free state resonance frequency $F_0$ of the flexural resonator is determined first. When the distal end of the oscillating metal rod 1 is applied to a substance, such as an area of tissue 3, the resonance frequency $F_R$ will change and the resonance peak width $\delta F$ will widen. The change in these values is a result of the damping effect of the mechanical impedance of the substrate, or tissue 3, being analyzed. The resonance peak width in free state is basically negligible because of the sharpness of the resonance peak when no damping occurs. Therefore, by measuring the resonance frequency of the flexural resonator after its oscillation has been damped by the impedance of the tissue 3 and determining the resonance peak width $\delta F$ caused by the damping, the mechanical properties of the tissue 3 in the direction of the angle of oscillation $\phi$ can be calculated.

The complex mechanical impedance Z of the tissue 3 is comprised of real (R) and imaginary (X) components and is determined by completing the equation:

$$Z = R + jX = k_1\, \delta F + jk_2\, (\Delta F_R),$$

where $\Delta F_R$ is the difference between the resonance frequency $F_R$ measured after applying the flexural resonator to the tissue 3 and the free state resonance frequency $F_0$, and where $k_1$ and $k_2$ are constant coefficients. The constant coefficients for a mechanical resonator are explained in Matheson, *Molecular Acoustics*, § 6.6 at pp. 102–104 (1971), which is incorporated herein by reference. The constant coefficients $k_1$ and $k_2$ can be approximated theoretically or by calibration of the flexural resonator with a material with known mechanical properties.

Based on the calculated mechanical impedance, the property of shear elasticity G of the tissue 3 at the same angle of oscillation $\phi$ is calculated by the formula:

$$G=(R^2-X^2)/\rho,$$

where $\rho$ is the density of the material, or tissue 3, being analyzed. Similarly, the dynamic viscosity $\eta$ is calculated as:

$$\eta=(2RX)/(\omega\rho),$$

where $\omega$ is the angular frequency of the tissue 3 and is determined by the formula $\omega=2\pi F$.

In a preferred embodiment, as shown in FIG. 6b, the measurements relating to the resonance frequency $F_R$ and the value of the resonance peak width $\delta F$ at each angle of oscillation $\phi$ derived through the phase-locked loop circuit and frequency detector 45 are stored in a memory unit 33 readily accessible by the microprocessor 30. The microprocessor 30 acts as the computing means to perform the above-defined calculations to determine the anisotropic mechanical properties. The computations are generally performed outside the outer case 10 of the hand-held probe by some processing means in the electrical module, but the use of an external computer, or even manual calculations could be used. Other means for computing the anisotropic mechanical properties from the values of resonance frequency $F_R$ and resonance peak width $\delta F$ will be apparent to those skilled in the art.

In a preferred embodiment, the tissue analyzer will be connected to a display unit 31 on the electrical module, capable of displaying both text and graphics at the same time. The display 31 is controlled by and receives data from the microprocessor 30 which determines the data to be displayed and the presentation of that data. One display unit which may be used for the application is a PD02-D104 Plasmadot DC Plasma 128×64 Dot Matrix Display System by Cherry Electrical Products in Waukegan, Ill. This display was chosen for its ability to display text and graphics at the same time. Other displays which may be utilized as well, include an LCD display, an oscilloscope, and a computer monitor. In fact, in some embodiments of the present device, the tissue analyzer has been connected directly to a computer, and the computer monitor has served as the display. The processing unit in the electrical module can be any processor, but preferably a microprocessor 30 is used, such as an 8-bit Intel microprocessor.

In a preferred embodiment, the display unit 31 will show a radial graph on which the anisotropic mechanical properties are plotted corresponding to each angle of oscillation $\phi$ at which the properties were determined. Other graphical representations can also be used, but the radial graph is often the most helpful in presenting the variations in the properties in different directions. The information relating to the anisotropic mechanical properties may also be displayed in chart form, or any other presentation that may be useful. Those skilled in the art will understand that many alternate forms of display units or graphical representations may be substituted and are equally applicable to the present invention.

Referring again to FIG. 6b which displays a circuit diagram wherein the electrical connections of a preferred embodiment are shown, those skilled in the art will readily appreciate the connections and operation of the circuit with the following brief description of the reference numerals. The circuit components include sensor input amplifiers 17, 17', amplitude detectors 18, 18', analog dividers 19, 25, a summing amplifier 20, a phase detector 21, a voltage controlled oscillator (VCO) 22, analog multipliers 23, 23', a correction amplifier 26, digital-to-analog converters (DAC) 27, 27', an analog-to-digital converter (ADC) 29, a microprocessor 30 and a display 31. A memory unit 33 is coupled with the microprocessor 30. The size of the memory unit 33 required is dependent on the amount of data to be stored and the amount of processing done directly in the microprocessor 30. Finally, the electrodes 5, 5', 6, 6' of the transducer 4 are connected as shown.

Figure 8:
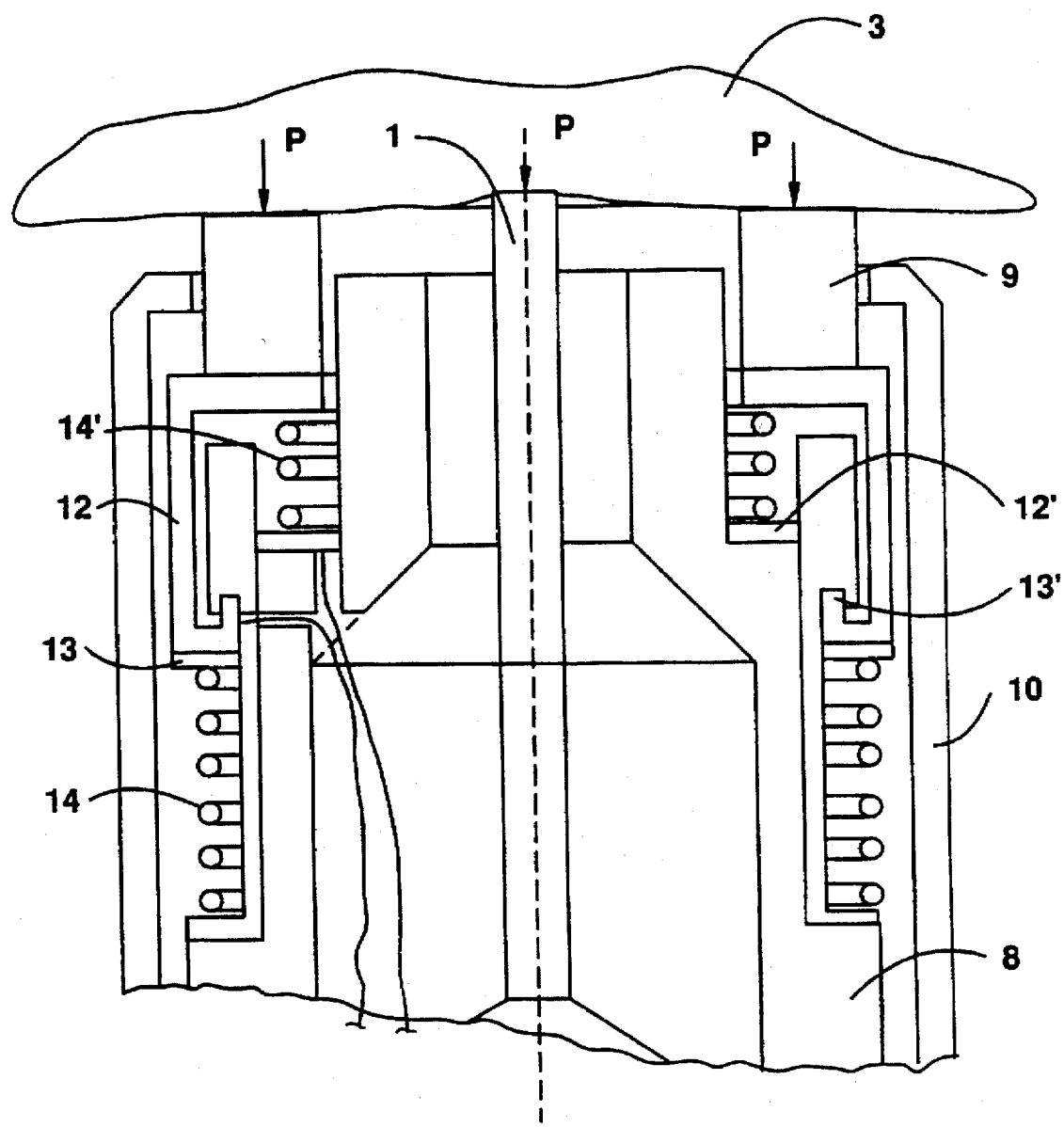
FIG. 8 is a cross-sectional view of a pressure normalizing element of the present invention.
Figure 9A:
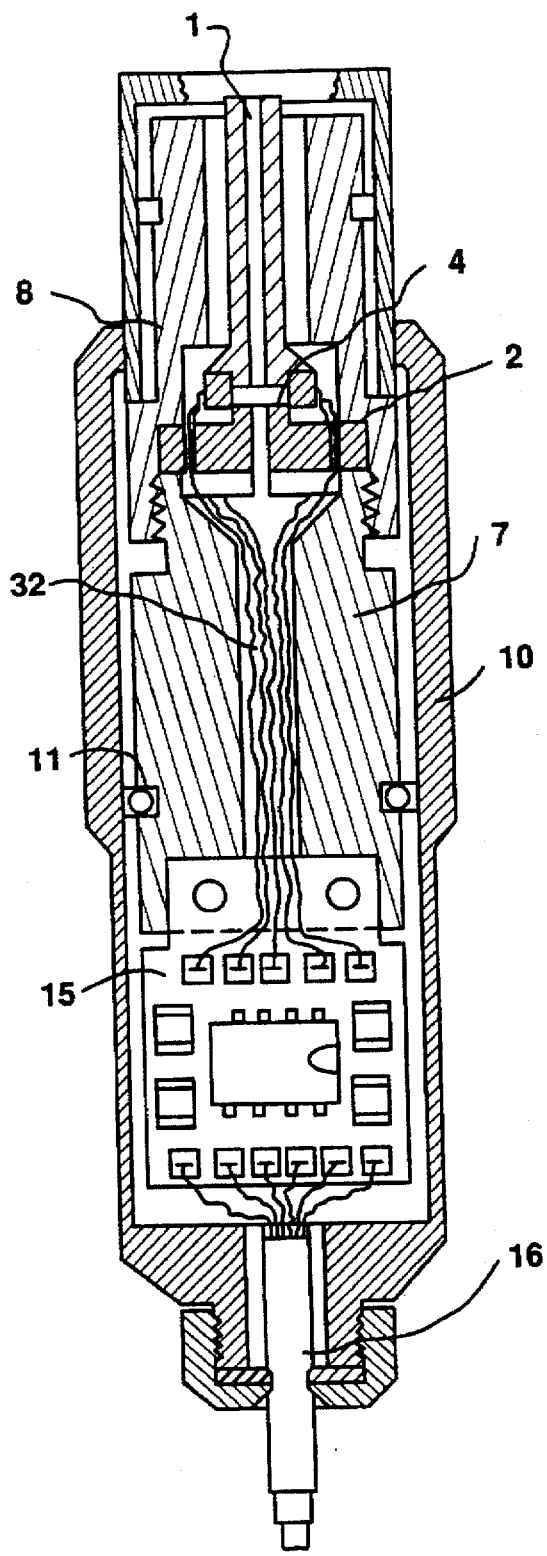
FIG. 9 is a cross-sectional view of a pressure normalizing element using a suction pump.
Figure 9B:
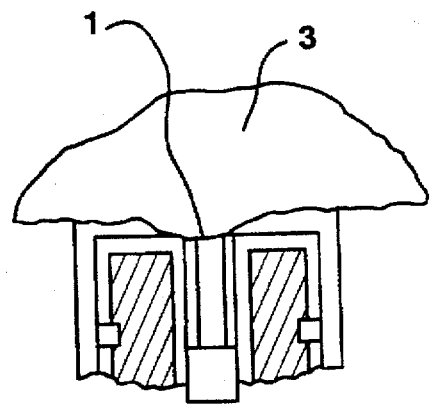
Figure 10:
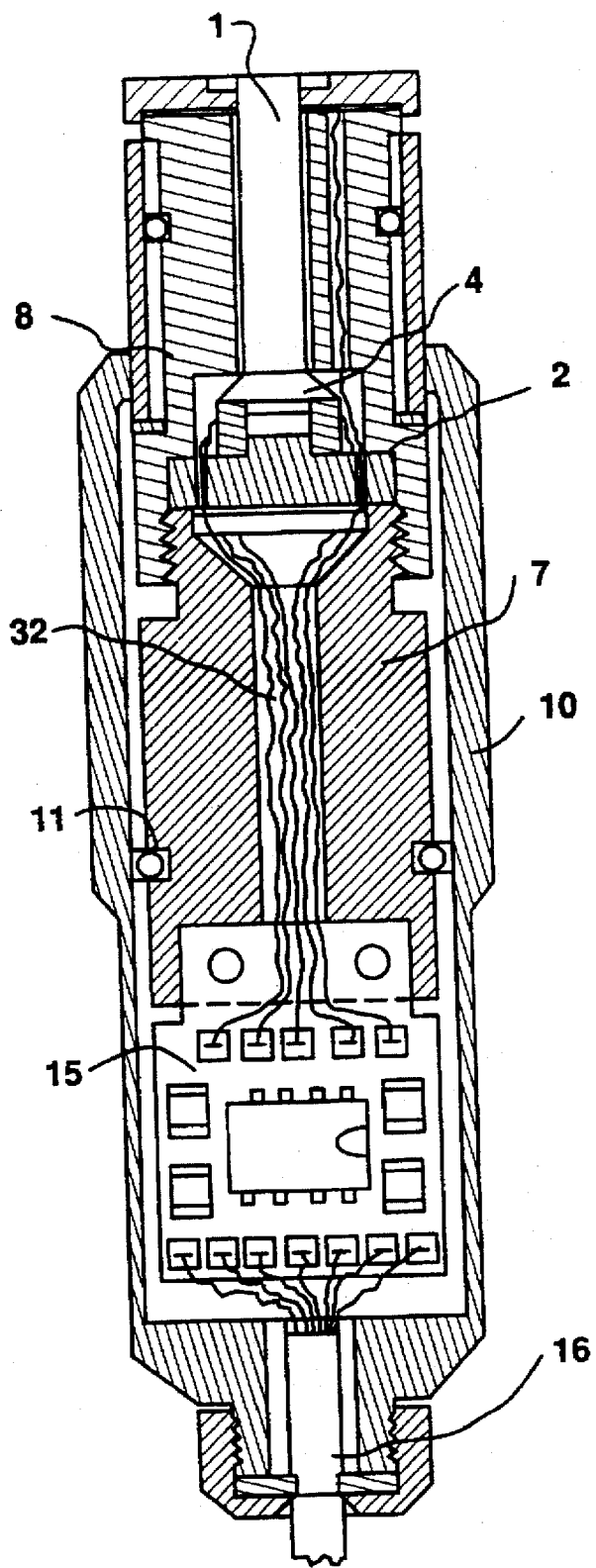
FIG. 10 is a cross-sectional view of a pressure normalizing element made of a pressure sensitive resistor film, which measures the pressure being applied by the distal end of a flexural resonator to the surface of tissue being analyzed to determine if an appropriate pressure is being maintained.

Finally, as explained above, the pressure normalizing element for use with the tissue analyzer of the present invention serves to provide a secure connection between the distal end of the metal rod 1 of the flexural resonator and the tissue 3 being analyzed. It also works to normalize the amount of force, or pressure, being applied by the metal rod 1 to the tissue 3 during the measurements to prevent variations in pressure which could effect the measurements of the resonance frequency and resonance peak width. Pressure normalizing elements are well-known in the art, as exemplified in U.S. Pat. Nos. 4,947,851 (Sarvazyan, et al.) and 5,115,808 (Popovic et al.) (the disclosures of which are hereby incorporated by reference). FIGS. 8–10 display cross-sectional views of the tissue analyzer of the present invention with emphasis on the pressure normalizing element used.

FIG. 8 displays a mechanical design for the pressure normalizing element. The metal rod 1 of the flexural resonator is shown with the distal end in contact with a surface of tissue 3 being analyzed. As described above, the metal rod 1 is enclosed in an outer case 10. The pressure normalizing element comprises pressure rings 9, moving contact rings 12, 13, fixed contact rings 12', 13', and springs 14. The pressure rings 9 come in direct contact with the tissue 3 to be analyzed and apply substantially the same pressure to the tissue 3 as does the distal end of the metal rod 1. The pressure rings 9 are rigidly affixed to the moving contact rings 12, which are supported by springs 14. The springs are supported by the support ring 8 which surrounds the flexural resonator. When the minimum contact pressure necessary for performing the required measurements is exerted by the pressure rings 8, the moving contact rings 12 electrically contact the fixed contact rings 13' and an electrical circuit is closed, thereby indicating that the required measurements can be taken. If the maximum contact pressure at which a measurement may be taken is exceeded, the pressure on the moving contact ring 13 supported by the spring 14 causes the electrical connection between the moving contact ring 13 and the fixed contact ring 13' to be severed. The electrical circuit is thereby opened, preventing further measurements from being taken. This embodiment of the pressure normalizing element, therefore, works to enable and disable the measuring function of the present invention based upon the amount of pressure exerted by the pressure rings 9 on the tissue 3. Therefore, the pressure during measurement will be standardized between the chosen minimum and maximum pressure values, which are sufficiently close that the pressure variations allowed do not adversely effect the frequency and peak width measurements of the present invention.

Another preferred embodiment of the pressure normalizing element is disclosed in FIG. 9. In FIG. 9, the same basic tissue analyzer device of FIG. 4 is shown. The metal rod 1 of the flexural resonator is still encompassed by an outer case 10 and supported by a support base 2 and various other support structures. In FIG. 9, however, the pressure normalizing element employs a suction pump which exerts negative pressure upon the surface of tissue 3 being analyzed. In this embodiment, there is a hole driven through the flexural resonator and a suction pump affixed near the support base 2 in the tissue analyzer. A tubing allows the suction pump to apply a negative pressure to the tissue 3. This negative pressure draws the surface of tissue 3 into contact with the distal end of the metal rod 1. During the measurements, the suction pump continues to exert a standard negative pressure upon the tissue 3 to secure the contact between the distal end of the metal rod 1 and the tissue 3, and to ensure that the pressure applied by the metal rod 1 is standardized.

A third embodiment of the pressure normalizing element is disclosed in FIG. 10. Here, the pressure normalizing element is comprised of a pressure sensitive resistor film which detects the pressure being applied by the distal end of the metal rod 1 against the tissue 3 being measured. There are a wide variety of force sensitive resistors that operate in generally the same fashion and are well-known in the art. One example which could be utilized with the present invention is the Force Sensing Resistance (FSR) from Interlink Electronics, of Camarillo, Calif. The pressure sensitive resistor film operates in basically the same manner as the mechanical pressure normalizing element described in connection with FIG. 8. In general, the element disables testing while the force being applied by the distal end of the flexural resonator is less than some predefined minimum force. When the minimum force, or pressure, is applied, an electrical connection is closed and the testing is enabled. Then, if the pressure exceeds a maximum allowable force, the testing again is disabled. Those skilled in the art will readily appreciate the electrical and chemical operation of this force sensitive resistor and its application in the method of the present invention.

As described above, yet another embodiment for the pressure normalizing element comprises a needle affixed to the distal end of the metal rod 1. The needle is inserted into the tissue 3 being analyzed so that the needle provides a secure connection between the metal rod 1 and the tissue 3. The needle also provides for evaluating the anisotropic mechanical properties of the tissue 3 beneath its surface layer. This application is preferred in connection with non-human tissue measurements.

Finally, to summarize the method of the present invention, FIG. 11 is a flowchart demonstrating the steps taken in performing a preferred method. Each of the steps has been described above in connection with the various components used in performing them. The flowchart of FIG. 11 provides for a succinct explanation of the method performed by the present invention. The method begins at step 101. First, the free state resonance frequency $F_0$ is determined for the oscillating flexural resonator at step 103. This step provides for measuring the resonance frequency while the flexural resonator is not in contact with any substance to be tested. In order to complete this determination, the transducer 4 causes the flexural resonator to oscillate. The phase-locked loop circuit identifies the resonance frequency of the flexural resonator, i.e. the free state resonance frequency $F_0$. The frequency detector 45 then measures the free state resonance frequency $F_0$ and transmits that value to be stored in the memory unit 33 of the electrical module.

Once the free state resonance frequency $F_0$ has been determined and stored, the method provides for applying the distal end of the metal rod 1 of the flexural resonator to a area of tissue 3 to be analyzed, at step 105. The amount of pressure applied to the tissue 3 by the distal end of the metal rod is then normalized at step 107. As explained in detail above, the pressure applied by the flexural resonator to the tissue 3 must remain within a predetermined range to ensure that variations in the pressure do not affect the frequency measurements and, thereby, the values determined for the mechanical properties. A pressure normalizing element, as described above in connection with FIGS. 8–10 performs this step of the preferred method.

Next, at step 109, a specific angle of oscillation $\phi$ to be used for testing is selected. Due to the anisotropic properties of the tissue 3 being measured, the mechanical properties of the tissue vary according to the direction, or angle, at which they are measured. Therefore, in order to accurately describe the mechanical properties of the tissue 3, the angle at which the properties were determined must accompany the value of the particular property. In a preferred embodiment, the method of the present invention will measure the mechanical properties of the tissue 3 being analyzed at a variety of angles of oscillation $\phi$, such that mechanical properties of the tissue 3 are determined at a sufficient number of angles between 0° and 180° to accurately define the anisotropic mechanical properties.

Once a specific angle of oscillation $\phi$ is selected at step 109, the flexural resonator, at step 111, is driven to oscillate at that angle of oscillation $\phi$ by the transducer 4. In a preferred embodiment, the oscillation at the selected angle of oscillation $\phi$ is controlled by variable voltages being applied to electrodes attached on the outer surface of the tubular piezotransducer, as described above. The ratio of the voltages at the transmitting electrodes 5, 6 control the angle of oscillation $\phi$. While the flexural resonator is oscillating at the selected angle of oscillation $\phi$, at step 113, the phase-locked loop circuit is employed to locate the resonance frequency $F_R$ of the flexural resonator at the selected angle of oscillation $\phi$ while in contact with the tissue 3 being analyzed and lock the oscillations into the resonance frequency $F_R$. Once the resonance frequency has been established, at step 115, the frequency detector 45 measures the resonance frequency $F_R$ thereby established.

In order to complete the required measurements at the selected angle of oscillation $\phi$, the resonance peak width $\delta F$ must be determined at step 117. Again, the procedure for determining the resonance peak width $\delta F$ is described above, in connection with FIGS. 6a and 6b. To summarize, the phase-locked loop can locate and lock in the frequency at +45° or −45° to measure the half power bandwidth, which is converted to resonance peak width by the formula provided above. Next, at step 119, the values of the resonance frequency $F_R$ and the resonance peak width $\delta F$ for the selected angle of oscillation $\phi$ are transmitted to the memory unit 33 for use in calculating the anisotropic mechanical properties of the tissue 3 being analyzed.

At step 121, the method provides for determining whether all of the angles of oscillation $\phi$ for which it is desired to calculate the mechanical properties of the tissue 3 have been selected. If not, then a different angle of oscillation $\phi$ is selected (again at step 109), and the same steps (step 111–119) are repeated with newly selected angles of oscillation $\phi$. The method preferably provides for selecting a sufficient number of angles of oscillation $\phi$ to accurately graph the mechanical properties to show the anisotropy of the tissue being analyzed. The angles are typically selected by a microprocessor according to software, wherein the software automatically cycles through a predefined set of angles. Once every desired angle of oscillation $\phi$ has been selected, as determined at step 121, the method continues at step 123.

In accordance with step 119, all of the necessary values for resonance frequency $F_R$ and resonance peak width $\delta F$ for each angle of oscillation $\phi$ at which the flexural resonator was oscillated have been stored in memory 33. With these values and using the formulae for mechanical impedance Z, shear elasticity G and dynamic viscosity $\eta$ provided above, the desired anisotropic mechanical properties for each angle of oscillation $\phi$ are calculated at step 123. It is readily apparent that the calculation of these mechanical properties can be performed at any time after the required measurements have been taken for each angle of oscillation $\phi$. Therefore, steps 121 and 123 may be performed in the reverse order, such that the mechanical properties corresponding to the selected angle of oscillation $\phi$ are calculated before the next angle is selected. Finally, the calculated values for the anisotropic mechanical properties are displayed at step 125. Again, preferably the properties are displayed as a radial graph with the calculated value of the mechanical property to be displayed plotted at the corresponding angle of oscillation $\phi$. However, other methods of display are also available and are within the contemplated scope of the invention.

In a preferred embodiment, the flowchart is implemented through software which is stored in the memory unit 33 and executed by the microprocessor 30 of the electrical module. Using the microprocessor embodiment, a complete analysis can be made in approximately three seconds. Other implementations of the method, however, are certainly possible and are contemplated to be within the scope of the following claims.

While the invention has been described and illustrated with reference to specific embodiments, those skilled in the art will recognize that modification and variations may be made without departing from the principles of the invention as described hereinabove and set forth in the following claims.

What is claimed is:

1. A method for measuring mechanical anisotropic properties of viscoelastic material comprising the steps of:

oscillating a flexural resonator by use of a transducer, such flexural resonator possessing a distal end adapted to be applied to a surface of viscoelastic material and a base end affixed to the transducer;

determining a free state resonance frequency of the oscillating flexural resonator;

placing the distal end of the flexural resonator on a viscoelastic material to be analyzed;

measuring a modified resonance frequency and a resonance peak width for the oscillating flexural resonator at a plurality of angles of oscillation upon the surface of viscoelastic material; and determining anisotropic mechanical properties of the surface of viscoelastic material based upon a difference between the free state resonance frequency and the modified resonance frequencies and based on the resonance peak widths for the oscillating flexural resonator at the plurality of angles of oscillation.

2. The method of claim 1 comprising the additional step of:

displaying a graphical representation of the mechanical properties of the viscoelastic material determined for each of the plurality of angles of oscillation, such graphical representation being indicative of anisotropic properties and degree of hardness.

3. The method of claim 1 comprising the additional steps of:

calculating a mechanical impedance of the surface of viscoelastic material for each of the plurality of angles of oscillation; and displaying the mechanical impedance of the surface of viscoelastic material for each of the plurality of angles of oscillation.

4. The method of claim 3 comprising the additional steps of:

determining a shear elasticity of the surface of viscoelastic material for each of the plurality of angles of oscillation based upon the mechanical impedance of the surface of viscoelastic material and a density of the surface of viscoelastic material being analyzed; and displaying the shear elasticity of the surface of viscoelastic material.

5. The method of claim 3 comprising the additional steps of:

determining a dynamic viscosity of the surface of viscoelastic material for each of the plurality of angles of oscillation based upon the mechanical impedance of the surface of viscoelastic material and a density of the surface of viscoelastic material and an angular frequency of the surface of viscoelastic material; and displaying the dynamic viscosity of the surface of viscoelastic material.

6. The method of claim 1 comprising the additional step of:

normalizing an amount of pressure applied by the distal end of the oscillating flexural resonator to the viscoelastic material with a pressure normalizing element.

7. The method of claim 6, wherein the pressure applied by the distal end of the oscillating flexural resonator to the surface of viscoelastic material is normalized between 10 and 500 grams.

8. The method of claim 1, wherein the oscillating flexural resonator of the viscoelastic material analyzer is oscillated at a frequency of between 0.5 and 10 kHz.

9. The method of claim 1, wherein a viscoelastic material analyzer is used to measure mechanical properties below the surface of viscoelastic material and wherein a needle is affixed to the distal end of the oscillating flexural resonator and is embedded in the viscoelastic material in order to obtain a better connection with the viscoelastic material to be analyzed and to measure the properties of the viscoelastic material under its surface layer.

10. A tissue analyzer for testing mechanical properties of viscoelastic material comprising:

a flexural resonator possessing a distal end which is adapted to be applied perpendicular to and in contact with a viscoelastic material to be analyzed and a base end;

at least one transducer element attached to the base end of the flexural resonator, for oscillating the flexural resonator at a plurality of angles of oscillation and for providing input related to resonance frequencies and resonance peak widths of the flexural resonator;

a processor unit for transmitting signals to the transducer element to control the angle of oscillation of the flexural resonator and for receiving input related to resonance frequencies and resonance peak widths of the flexural resonator;

a phase-locked loop circuit for obtaining input data relating to the resonance frequencies and resonance peak widths of the flexural resonator at each of the plurality of angles of oscillation and for transmitting the input data to the processor unit;

a memory unit readily accessible to the processor unit for storing the input data and instructions;

a calculator means for determining specific mechanical properties of the viscoelastic material being analyzed by manipulating the input data, retrieved from the memory unit, relating to the resonance frequencies and resonance peak widths of the flexural resonator; and a display, for displaying values of the mechanical properties of the viscoelastic material at the plurality of angles of oscillation.

11. The viscoelastic material analyzer of claim 10 further comprising:

a pressure normalizing element, attached to a support ring surrounding the distal end of the flexural resonator, for normalizing an amount of force to be applied by the distal end of the flexural resonator when in contact with the viscoelastic material to be analyzed.

12. The viscoelastic material analyzer of claim 10 further comprising:

a pressure normalizing element comprising a sharp element affixed to the distal end of the flexural resonator, such sharp element adapted to be inserted into the viscoelastic material being analyzed and to normalize an amount of force to be applied by the distal end of the flexural resonator when in contact with the viscoelastic material.

13. The viscoelastic material analyzer of claim 10 further comprising:

a pressure normalizing element comprising a suction pump affixed to the base end of the flexural resonator, such suction pump adapted to apply negative force to the viscoelastic material being analyzed thereby normalizing an amount of force to be applied by the distal end of the flexural resonator when in contact with the viscoelastic material.

14. The viscoelastic material analyzer of claim 10, wherein the flexural resonator is cylindrical in shape.

15. The viscoelastic material analyzer of claim 10, wherein the transducer element is a radially polarized tubular piezotransducer.

16. The viscoelastic material analyzer of claim 15, wherein the tubular piezotransducer is driven by exactly two pair of electrodes affixed to an outer surface of the tubular piezotransducer.

17. The viscoelastic material analyzer of claim 10 further comprising:

a communication port connected to the memory unit for transmitting data to and receiving data from an external source.

* * * * *